United States Patent
Peerless et al.

[11] Patent Number: 5,851,199
[45] Date of Patent: Dec. 22, 1998

[54] OTOLOGICAL DRAIN TUBE

[76] Inventors: Sidney A. Peerless, 3131 Harvey Ave., Cincinati, Ohio 45229; Joseph C. Burge, 1 Rabbits Run, Palm Beach Gardens, Fla. 33418

[21] Appl. No.: 949,466

[22] Filed: Oct. 14, 1997

[51] Int. Cl.$^6$ .................................................. A61M 5/00
[52] U.S. Cl. ............................................. 604/8; 606/109
[58] Field of Search ......................... 604/8–10; 606/108, 606/109, 264, 27, 30, 43, 45

[56] References Cited

U.S. PATENT DOCUMENTS

| | | |
|---|---|---|
| 3,897,786 | 8/1975 | Garnett et al. . |
| 3,913,584 | 10/1975 | Walchle et al. . |
| 3,976,081 | 8/1976 | Lapidot ..................................... 128/350 |
| 4,094,303 | 6/1978 | Johnston . |
| 4,168,697 | 9/1979 | Cantekin . |
| 4,174,716 | 11/1979 | Treace . |
| 4,175,563 | 11/1979 | Arenberg et al. ............................ 604/9 |
| 4,473,073 | 9/1984 | Darnell . |
| 4,568,337 | 2/1986 | Treharne, III et al. ...................... 604/9 |
| 4,650,488 | 3/1987 | Bays et al. ................................. 623/12 |
| 4,712,537 | 12/1987 | Pender . |
| 4,744,792 | 5/1988 | Sander et al. . |
| 4,808,171 | 2/1989 | Berger . |
| 4,964,850 | 10/1990 | Bounton et al. . |
| 5,026,378 | 6/1991 | Goldsmith, III ......................... 606/109 |
| 5,053,040 | 10/1991 | Goldsmith et al. . |
| 5,137,523 | 8/1992 | Peerless et al. . |
| 5,304,192 | 4/1994 | Crouse . |
| 5,308,357 | 5/1994 | Lichtman . |
| 5,489,286 | 2/1996 | Cinberg et al. .......................... 606/109 |
| 5,496,329 | 3/1996 | Reisinger ................................. 606/109 |
| 5,643,280 | 7/1997 | Del Rio et al. . |
| 5,645,584 | 7/1997 | Suyama ..................................... 623/10 |

*Primary Examiner*—John G. Weiss
*Assistant Examiner*—Ki Yong O
*Attorney, Agent, or Firm*—Norman Friedland

[57] ABSTRACT

An otological drain tube which is capable of being implanted in the ear drum to vent the differential pressure that can build up across the ear drum as the result of blocked eustachian tubes, a buildup of internal liquid pressure in the inner ear due to illness, or a change in atmospheric pressure. The otological tube comprising: a cap-plug, a central body, an end cap. And a means for permanently securing the elements together. The assembly of these elements creates a plurality of lumens of a requisite cross sectional area within the otological drain tube body. The primary object of the invention is to produce an otological drain tube which is extremely effective and economical to produce.

11 Claims, 3 Drawing Sheets

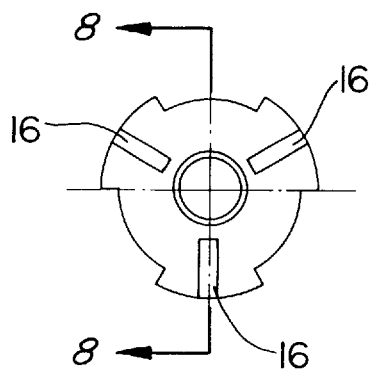
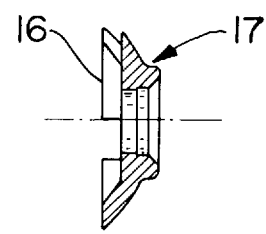
FIG. 7   FIG. 8
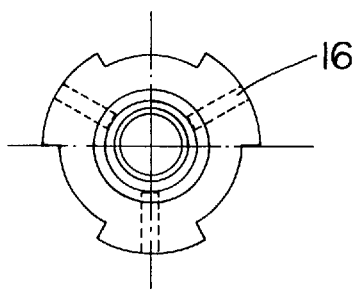
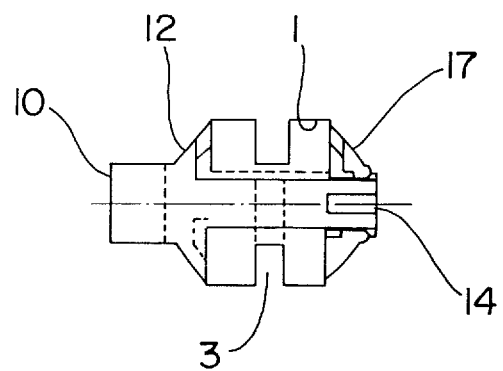
FIG. 9   FIG. 11
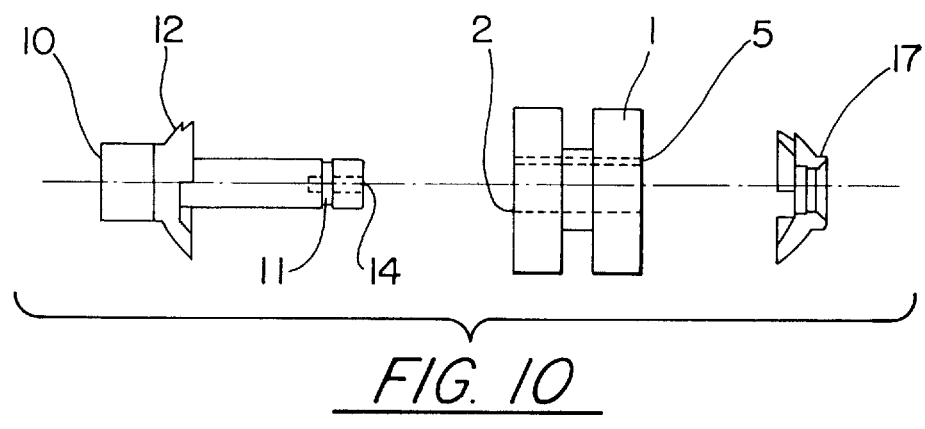
FIG. 10

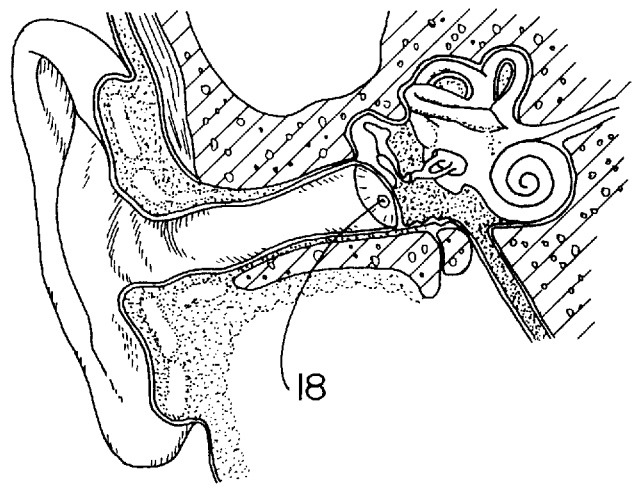
FIG. 12
FIG. 13
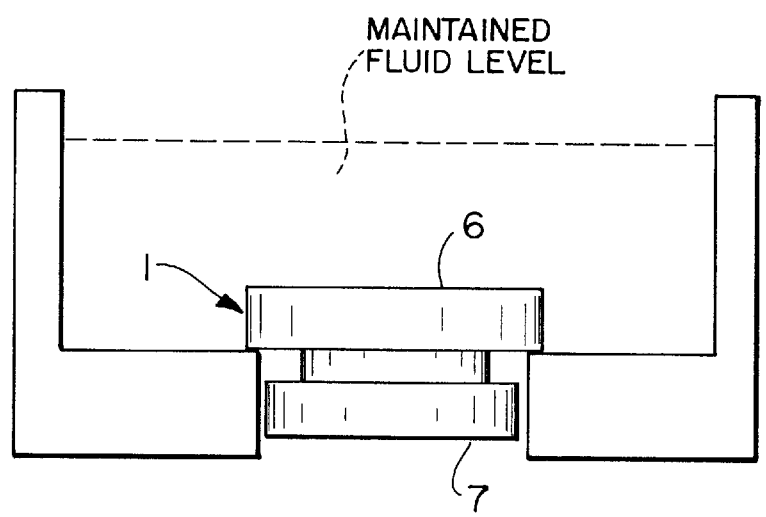
FIG. 14

OTOLOGICAL DRAIN TUBE

TECHNICAL FIELD

This invention relates to otological drain tubes which are capable of being implanted in the ear drum to vent the differential pressure which builds up across the ear drum as the result of blocked eustachian tubes, a buildup of internal liquid pressure due to illness, accident, or a change in atmospheric pressure. This invention is an improvement which results in a reduced cost to manufacture, and a simplified assembly procedure over the prior art referenced herein.

BACKGROUND ART

Otological drain tubes are not new. The original concept was formulated by Dr. Politzer in 1863 wherein his tubes were manufactured of hard rubber. Dr. Politzer's design used lumens which had a diameter of 0.049 inches. It is not known whether Dr. Politzer's 0.049 diameter was obtained empirically, or used simply because the drill technology in 1863 limited the practical minimum bore size. During the past 134 years, many designs for Otological drain tubes have emerged. The diameter of the lumens has not significantly changed. The cross section of the lumens has been held at 0.040 to 0.052 inches. There are designs for otological drain tubes which contain a single passageway for air or fluid, and others have evolved which utilize a plurality of such passageways. These passageways are also called lumens.

Typical of the kind of otological drain tubes that have been patented is U.S. Pat. No. 5,137,523 granted on Aug. 11, 1992 to Peerless and Burge, who are co-inventors of the present application. Their U.S. Pat. No. 5,137,523 is incorporated herein by reference. The U.S. Pat. No. 5,137,523 reveals an otological drain tube for implanting in an ear drum, and is manufactured from metals such as stainless steel or titanium, and which requires expensive machining processes due to the small size of the otological drain tube. The U.S. Pat. No. 5,137,523 also teaches a lumen size in the order of 0.004 to 0.005 inches.

Research during the process of developing the otological drain tubes as taught in the referenced U.S. Pat. No. 5,137, 523 has revealed that the 0.049 diameter was not the optimum size which can achieve the desired goals of performance for the otological drain tube. Diameters in the order of 0.004 to 0.005 inch, with 0.005 inch as the preferred dimension, perform extremely well.

The question arose of whether the reduction in lumen size from 0.049 to 0.004 inch was justified and technically sound. This was a reasonable question and the answer is the heart of the referenced invention. Quantitative analysis and measurements were first taken on the smallest lumen, a 0.004 inch diameter bore, 0.085 inch in length. If this size could fulfill the performance goals, then the 0.005 inch lumen would also prove to be equally acceptable.

A single 0.004 inch lumen was tested for flow capability under these conditions, and found to pass 125 CC of fluid within 24 hours, when saline solution (mimicking the substance found in the ear), was applied to the flow rate test fixture. A single lumen of 0.004 inch will drain the fluid in the ear in approximately 15.75 minutes. A single 0.005 in lumen will drain this volume of fluid in the inner ear in approximately 10 minutes. The conclusion was that a single lumen of 0.004 inches has more than sufficient flow capacity to drain the fluid which can build up in an infected ear. The lumen is oversized by an order of magnitude more for air than it is for liquid. In most cases, however, the relief of pressure related pain occurs immediately, as the internal hydrostatic or air pressure is reduced. These new lumen dimensions are patented in the referenced invention, U.S. Pat No. 5,137,523.

Modern Otological drain tubes, also referred to as Tympanotomy tubes or Myringotomy tubes have been manufactured from Stainless Steel or Titanium, or from other inert materials such as hard rubber or plastics. Simple otological drain tubes have been produced from plastics, these being likened to a grommet design, having a single central bore of 0.049 inches and flanges on each end. An example of this prior art, an otological drain tube manufactured by Xomed-Treace, is shown in FIG. 13.

Otological drain tubes are extremely small, and they require a high degree of precision during manufacture. The drain tubes are installed by a surgeon who makes a small incision into the tympanic membrane (the ear drum), he then inserts the otological drain tube in the incision, until the otological drain tube is in place. The otological drain tubes are designed to provide a passage for air or liquid to pass out of the inner ear, thus reducing the internal pressure within. The reduction of pressure relieves the pain associated with the inflammatory disorder. Many Otological drain tubes have been designed to perform this function, but their manufacture from metals has increased their cost. The presence of a large lumen (e.g.) 0.049 inches, allows liquids and dirt particles to enter the inner ear through the opening. Other designs have included shields for the lumens and have included membrane type valves to protect from inflow of particulate matter.

The otological drain tube of the referenced prior art, U.S. Pat. No. 5,137,523, hereinafter called the Peerless/Burge tube, has reduced the maximum size of the lumen to 0.005 inches, and thus offers greater protection against entry of foreign material into the inner ear. In addition, the end caps of the instant invention further isolate the lumens from entry of particulate matter.

The foregoing details have been included as background information and are not included as material pertinent to the instant patent application.

Additional Prior Art can be Found in the Following U.S. Patents:

U.S. Pat. No. 4,808,171 V Shaped Ear Ventilation Tube granted in Feb. 19, 1989 to Berger; U.S. Pat. No. 4,964,850 Method for Treating Trans-nasal Sinus Afflictions Using a Double T-shaped Trans Nasal Aerator granted in October 1990, to Bounton et al.; U.S. Pat. No. 4,695,275 Middle Ear Ventilation Tube granted in October 1987 to Bruce et al.; U.S. Pat. No. 4,174,716 Myringotomy Tube granted November 1979 to Treace; U.S. Pat. No. 4,712,537 Apparatus for Treating Recurrent Ear Infections granted December 1987 to Pender; U.S. Pat. No. 4,744,792 Middle Ear Ventillating Tube granted May 1988 to Sander et al.; U.S. Pat. No. 4,094,303 Tympanic Membrane Vent granted June 1978 to Johnston; U.S. Pat. No. 4,168,697 Middle Ear Ventillating Tube and Method granted September 1979 to Cantekin; U.S. Pat. No. 3,913,584 Combination Myringotomy Scalpel, Aspirator and Otological Vent Tube Inserter. granted October 1975 to Walchle et al.; U.S. Pat. No. 5,304,192 Lancet with Locking Cover granted April 1994 to Crouse; U.S. Pat. No. 4,473,073 Myringotomy Tube Inserter and Method for Inserting Myringotomy Tubes granted September 1984 to Darnell; U.S. Pat. No. 3,897,786 Disposable Myringotomy Apparatus granted August 1975 to Garnett et al.; U.S. Pat. No. 5,053,040 Method of Performing a Myringotomy granted October 1991 to Goldsmith, et al.; U.S. Pat. No. 5,308,357 Handle Mechanism for Manual Instruments granted May 1994 to Lichtman; U.S. Pat. No. 5,643,280 Integral Myringotomy Tube and Inserter granted July 1997 to Del Rio et al.

Prior art modern Otological drain tubes for example, U.S. Pat. No. 5,137,523, granted August 1992, to Peerless et al. employ a plurality of lumens for passing air or fluid out of the inner ear., thus eliminating the pain which is caused when there is a differential pressure across the ear drum. In addition, the small lumens prevent fluid outside of the ear from entering the inner ear while allowing the internal fluids which are at a lower viscosity to flow outward. This configuration presented therein allows topical medications to be applied to the inner ear through the otological drain tube while minimizing the possibility of extraneous fluids, such as water, from entering the inner ear during swimming or bathing.

DISCLOSURE OF THE INVENTION

An object of the invention is to provide an Otological drain tube in which the lumens, the passageways which pass either air or ear fluid out of the inner ear are maintained at a small size, preferably a diameter equivalent of 0.005 inches, with the appropriate length to diameter ratio of 17, as defined in the referenced prior art, U.S. Pat. No. 5,137,523 granted to Peerless and Burge, the inventors of the instant invention.

It is an object of the invention is to provide an Otological drain tube which is easy to manufacture, is easy to install and use, and whose manufacturing process cost is greatly reduced from the referenced prior art. Costs to manufacture the invention described herein are typically one sixth of the cost to manufacture an otological tube of the referenced metal prior art. For example, when compared to the previously patented prior art, U.S. Pat. No. 5,137,523 by Peerless et al, supra, a reduction in manufacturing cost by 83.3 percent is achieved.

The otological drain tube of the instant invention is assembled from injection molded thermo plastic components. These components are assembled and then ultrasonically or thermally staked. If desired, the end cap and the plug can be permanently joined by chemically welding the parts together at the locking slot. Which is part of the central plug. Only one joint needs to be joined or staked, permanently holding the entire assembly together. After joining or staking, the entire assembly is plated by vapor deposition with either stainless steel or titanium. It is preferred, but not essential, that the injection molding material be doped to be slightly electrically conductive to assist the electronic vapor deposition metalizing process.

Recognizing that injection molded materials are more compliant than the metal components of prior art, pressures applied to the first and second end caps may cause the otological drain tube end cap to distort, and thereby restrict the flow of air or liquid to the drain lumens. Such distortion may inhibit or prevent proper draining. The instant invention contains a series of six standoff posts, three on each end cap, which prevent closure of the otological tube flow path when pressurized.

It is another object of this invention to provide an Otological drain tube which is manufactured of a minimum number of parts, and which can be assembled by machine. It is an object of this invention to provide an Otological drain tube which can be gas sterilized. It is a further object of this invention to provide an Otological drain tube with sufficient volumetric flow capacity such that the inner ear volume of a child or adult can quickly vent during all normal activities, thus relieving the pressure differential across the tympanic membrane.

BRIEF DESCRIPTION OF THE DRAWINGS

FIG. 7 is the front end view of the second end cap;

FIG. 8 is view A—A through the second end cap;

FIG. 9 is a view from the rear or forward most side of the second end cap;

FIG. 10 is an exploded view of the assembly of the otological tube. The cap-plug is inserted into and through the central body, and the second end cap is installed on the plug body and secured in place.

FIG. 11 illustrates the total otological drain tube assembly;

FIG. 12 shows the otological drain tube installed in the tympanic membrane, or ear drum, and FIG. 13 illustrates an example of a plastic otological tube of the prior art.

FIG. 14 illustrates the manner in which the otological drain tube is installed a flow test fixture. The scale of the drawing has been intentionally distorted to show the role that the larger face of the central body plays in the fixturing process.

BEST MODE FOR CARRYING OUT THE INVENTION

The Otological drain tube of the instant invention is assembled by slidably positioning three pre molded plastic component elements which are assembled with specific relationship to each other as shown in FIGS. 10 and 11.

Figure 3:
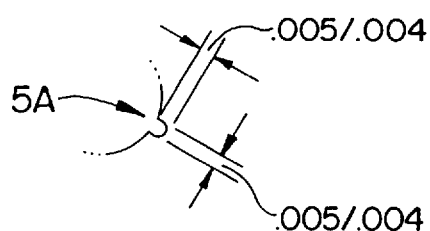
FIG. 3 is a detail, showing the lumens as viewed on the face of the central body bore.
Figure 4:
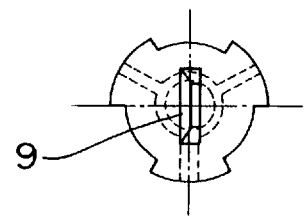
FIG. 4 is a view of the first end of the cap-plug as seen from the first cap outer end.
Figure 5:
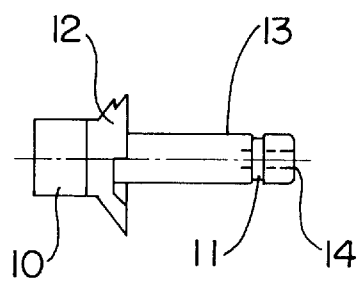
FIG. 5 is the side view of the cap-plug showing details of the first end cap which is integrally molded to the plug section, the total molded assembly being called a cap-plug.
Figure 6:
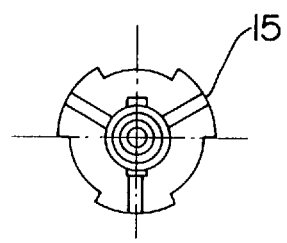
FIG. 6 is the view as seen when looking along the plug section of the cap-plug showing the standoff posts which prevent the end cap from closing against the central body when pressure is applied.

The invention is best understood by referring to FIGS. 1 through 10. These figures show the component elements and the assembly procedure. The component elements consist of a central body 1, a cap-plug which consists of a first end cap 12, and a plug body 13, integrally molded together, and a second end cap 17. The complete cap-plug is shown in FIG. 5. The central body further having a bore 2 therethrough, and in accordance with this invention a plurality of lumen passages 4 and 5 are inscribed on the circumference of the bore 2. The lumens are not formed until the cap-plug is inserted through the central body, where the lumens are formed by the lumen passages which are formed between the cap-plug and the central body.

FIG. 4 shows one of the lumens 4 which are extended completely through the length of the central body 1 from the first end 6 to the second end 7. The length of the central body is maintained at 0.085 inch.

Figure 2:
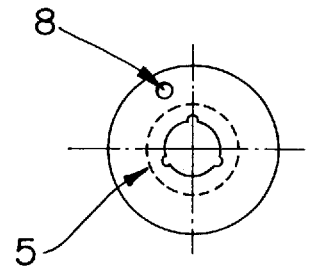
FIG. 2 is the end view of the second end of the central body of the otological drain tube.

Lumens may be formed by drilling or by broaching the bore 2 therethrough, or the lumens may be incorporated in the mold which produces the central body. The preferred method is to include the lumen passages in the mold. FIG. 2 shows the frontal end view of the central body, revealing the identifying dimple 8, and the lumen passageways. Although a plurality of such lumens may be used, the small size of the central body forces the optimum number of lumens ro be three, as shown.

When broached or incorporated in the mold, the lumens are generally "D" shaped, the detail of which can be seen in FIG. 3, which is a the view of section A—A, as depicted in FIG. 2. It is to be recognized by those skilled in the art that any shape which can be successfully molded or broached can be used during the manufacturing process. Said lumens each having a cross sectional area equivalent to a round diameter of 0.004 inches to 0.005 inches. The preferred lumen cross section area is made to be equivalent to a circular bore having a diameter of 0.005 inch. (A cross sectional area of 0.0000196 square inch). The length to diameter is held at a value of 17 to assure laminar flow therethrough.

Figure 1:
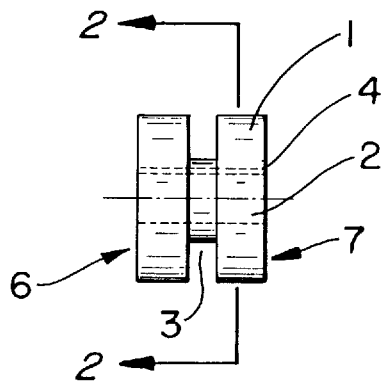
FIG. 1 is a side elevation view of the central body of the otological drain tube. In this view the lumens are described as item 4. The same lumens are described as item 5 in the other views.

The central body 1 also having a groove 3 in the outer periphery, as shown as item 3 in FIG. 1, for implanting the otological drain tube in the tympanic membrane of the ear, in an incision made by a surgeon. The lumen body length to diameter, (the L/D ratio) and the implanting groove are described in the referenced U.S. Pat. No. 5,137,523, granted to the inventors of the instant invention, Peerless et al.

The central 1 body further having a feature which is designed to facilitate testing of the otological drain tube. The central body 1 having a first end 6 and a second end 7, wherein the second end 7 is dimensioned to be 0.003 inch smaller in diameter than the first end. The central body is designed so that the first and second ends have different diameters such that the otological drain tube assembly will fit into a flow test fixture in one direction only. FIG. 14 illustrates how the otological drain tube of the present invention fits into the test fixture.

The test fixture, which is not part of the instant invention, is essential for assuring that the lumens 4 and 5 function properly, and have not been obscured during the vapor deposition process, as will be disclosed below.

Flow testing is abundantly important in accordance with this invention, since the component parts are extraordinarily small, and the lumen size is minuscule. A flow test fixture, shown in FIG. 14 is utilized to perform a well known flow test to assure that the lumens operate properly, passing either air or liquid at the proper rate.

The purpose of having a smaller end 7 on the central body 1 is to assure that the central body does not fall through the opening in the test fixture during the flow test, FIG. 14, which is not to drawn to scale, exemplifies the manner in which the flow test is performed.

The second end face 7 of the central body 1 also having a dimple 8 for identification purposes only. The cap-plug consists of a first end cap 12 and a plug portion 13. The plug portion having a first end and a second end, the first end of the cap-plug having the first end cap 12 integrally molded thereon. The first end cap further having a holding tab 10 molded thereon as part of the outer portion of the first end cap body, and having a plurality of standoff posts 15 on the inner surface of the first end cap section. The second end of the cap-plug having a notch 11 for locking a second end cap 17 onto the second end of the plug 13 body, the second end of the plug also having a blind counter bore 14 therein, for staking purposes. The preferred methods for staking include ultrasonic means or by thermal means. The second end cap may also be secured to the plug body 13 by chemical welding.

During assembly (as illustrated in FIG. 10) the cap-plug body 13 is inserted into the central body 1 first end 6, passing through the entire central body opening 2. The cap-plug is then slidably positioned within the central body 1 wherein the second end of the cap-plug 13 exits the central body second end 7, allowing the locking groove 11 to be exposed. The second end cap 17 is then slidably positioned on the second end of the plug 13 until the end cap 17 snaps into the locking groove 11, contained thereon. The first end cap 12 and the second end cap 17, are both fitted with standoff posts 15 on the first end cap, and 16 on the second end cap. The standoff posts are dimensioned and located such that they cannot interfere with the lumens 4 and 5, and thereby restrict the flow through the otological drain tube.

After the end cap 17 is installed on the plug body, and snapped into the locking groove, 11 and locked in place, the cap-plug 13 and the second end cap 17 are joined together by ultrasonic or by thermal staking of the pre-formed opening 14 in the plug body 13 or by chemical bonding of the end cap 17 to the plug body 13. The otological drain tube is then in fully assembled condition, and is seen in FIG. 11. Once assembled, the entire otological drain tube is then vacuum deposition plated with stainless steel or titanium. After plating, and immediately before final packaging, the gas sterilization process mat be repeated if deemed necessary.

The first end of the cap-plug 12 also contains an insertion tab 10 which the surgeon can use to implant the Otological drain tube into the tympanic membrane of the ear. The surgeon cuts a tiny incision into the tympanic membrane. The surgeon then inserts the Otological drain tube into the incision in the tympanic membrane, and then surgically inserts the body of the otological drain tube until the tympanic membrane falls into the central body groove 3 of the central body 1.

Although this invention has been shown and described with respect to detailed embodiments thereof, it will be appreciated and understood by those skilled in the art that various changes in form and detail thereof may be made without departing from the spirit and scope of the claimed invention.

We claim:

1. An otological drain tube which is capable of being implanted in the ear drum to vent the differential pressure that can build up across the ear drum as the result of blocked eustachian tubes, a buildup of internal liquid pressure in the inner ear due to illness, or a change in atmospheric pressure, the otological tube comprising: a central body, a cap-plug which consists of a first end cap and an integrally molded plug body, a second end cap, and a means for permanently securing the elements together when assembled, wherein the assembly of these elements creates a plurality of lumens within the central body, wherein the cross-sectional area of each lumen is equal to 0.00001257 to 0.0000196 square inches, and further having the first and second end caps containing therein integral support posts which are positioned to prevent the end caps from closing against the central body when pressure is applied to the end cap outer face, the first and second end caps further preventing particulate matter from entering the otological drain tube without impeding the flow of air or liquid therethrough, the otological drain tube being manufactured of plastic material which is inexpensively molded, sterilized, and plated with a protective metal coating.

2. The otological drain tube of claim 1, whereby the elements are composed of thermo plastics, selected from the group consisting of Teflon, Silicone, PTFE, H/C flex, Celcon, and Delrin.

3. The otological drain tube of claim 1, whereby the final assembly is electro plated by vacuum deposition with a metal selected from the group consisting of stainless steel, and titanium.

4. The otological drain tube of claim 1, whereby the assembly of the elements may be performed by machine.

5. The otological drain tube of claim 1, whereby the cost to manufacture is significantly less, and typically 16 percent of heretofore known otological drain tubes of metallic construction.

6. The otological tube of claim 1, wherein the drain tube central body contains a plurality of separate lumens and end caps, each end cap containing a plurality of support posts, wherein the lumens are sized to prevent particulate matter from entering the otological drain tube wherein, one lumen is sufficient to perform the drain requirements of the otological drain tube.

7. The otological drain tube of claim 1, whereby the otological drain tube can be gas sterilized.

8. The otological drain tube of claim 1, whereby the Assembly can be installed in a flow test fixture for testing the flow rate to assure lumen performance.

9. The otological drain tube of claim 1, wherein the flow test fixture can measure air flow rate, liquid flow rate, or whether the lumens are open.

10. The otological drain tube of claim 1 whereby the second end cap and the plug elements may be secured by ultrasonic staking or chemical welding.

11. The otological drain tube of claim 1 whereby the second end cap and the plug elements may be secured by thermal staking.

* * * * *